US011555171B2

(12) United States Patent
Frey et al.

(10) Patent No.: US 11,555,171 B2
(45) Date of Patent: Jan. 17, 2023

(54) MICROTISSUE COMPARTMENT DEVICE

(71) Applicants: INSPHERO AG, Schlieren (CH); ETH Zurich, Zurich (CH)

(72) Inventors: Oliver Frey, Oberwil (CH); Sebastian Bürgel, Zug (CH); David Fluri, Schlieren (CH); Jens Kelm, Schlieren (CH); Jin-young Kim, Deagu (KR)

(*) Notice: Subject to any disclaimer, the term of this patent is extended or adjusted under 35 U.S.C. 154(b) by 0 days.

(21) Appl. No.: 16/624,176

(22) PCT Filed: Jul. 9, 2018

(86) PCT No.: PCT/EP2018/068553
§ 371 (c)(1),
(2) Date: Dec. 18, 2019

(87) PCT Pub. No.: WO2019/008189
PCT Pub. Date: Jan. 10, 2019

(65) Prior Publication Data
US 2020/0208088 A1 Jul. 2, 2020

(30) Foreign Application Priority Data
Jul. 7, 2017 (GB) .................... 1710955

(51) Int. Cl.
C12M 1/32 (2006.01)
C12M 1/00 (2006.01)
C12N 5/071 (2010.01)
G01N 33/50 (2006.01)

(52) U.S. Cl.
CPC ............ C12M 23/12 (2013.01); C12M 27/18 (2013.01); C12N 5/0697 (2013.01); G01N 33/5014 (2013.01); G01N 33/5082 (2013.01)

(58) Field of Classification Search
CPC ...... C12M 23/12; C12M 27/18; C12M 23/16; C12M 21/08; C12N 5/0697; G01N 33/5014; G01N 33/5082
See application file for complete search history.

(56) References Cited

U.S. PATENT DOCUMENTS

| 5,650,323 A * | 7/1997 | Root | B01L 3/5085 210/238 |
| 7,897,377 B2 | 3/2011 | Stoppini | |
| 2003/0044971 A1 * | 3/2003 | Lyman | C12M 23/10 435/305.1 |
| 2005/0101010 A1 | 5/2005 | Li | |
| 2005/0277125 A1 * | 12/2005 | Benn | B01J 19/0046 435/6.11 |
| 2011/0117634 A1 | 5/2011 | Halamish et al. | |
| 2012/0328488 A1 * | 12/2012 | Puntambekar | B01L 3/5085 422/503 |
| 2014/0179561 A1 | 6/2014 | Takayama et al. | |

FOREIGN PATENT DOCUMENTS

| GB | 2507744 A | 5/2014 | |
| GB | 2539935 A | 1/2017 | |
| WO | WO-2014/083555 A1 | 6/2014 | |
| WO | WO-2016069917 A1 * | 5/2016 | .......... C12N 5/0062 |
| WO | WO-2016/166315 A1 | 10/2016 | |
| WO | WO-2019/008189 A1 | 1/2019 | |

OTHER PUBLICATIONS

Tonar et al. "Orientation, anisotropy, clustering, and volume fraction of smooth muscle cells within the wall of porcine abdominal aorta." Applied and Computational Mechanics 2 (2008) 145-156 (Year: 2008).*
Hsiao, A. Y. et al. "Microfluidic system for formation of PC-3 prostate cancer co-culture spheroids", Biomaterials 30, 3020-3027 (2009).
Kelm J et al. "Method for generation of homogeneous multicellular tumor spheroids applicable to a wide variety of cell types", Biotechnology and Bioengineering, 83(2) 173-180 (2003).
Kim et al., "3Dspherical microtissues and micro fluidic technology for multi-tissue experiments and analysis", pp. 24-35. J of Biotechnology, vol. 205, Jan. 2015.
Kim et al., "96 wellformat based microfluidic platform for parallel interconnection of multiple multicellular spheroids", J of Laboratory Automation, vol. 20, No. 3, Dec. 2014, pp. 274-282.
Kwapiszewska, K.et al. "A microfluidic-based platform for tumour spheroid culture, monitoring and drug screening", Lab Chip 14, 2096-2104 (2014).
Maschmeyer, I. et al. "A four-organ-chip for interconnected long-term co-culture of human intestine, liver, skin and kidney equivalents", Lab Chip 15, 2688-2699 (2015).
Occhetta, P. et al. "High-Throughput Microfluidic Platform for 3D Cultures of Mesenchymal Stem Cells, Towards Engineering Developmental Processes" Sci. Rep. 5, 10288 (2015).
Ruppen, J. et al. "A microfluidic platform for chemoresistive testing of multicellular pleural cancer spheroids", Lab Chip 14, 1198-205 (2014).
Ruppen, J. et al. "Towards personalized medicine: chemosensitivity assays of patient lung cancer cell spheroids in a perfused microfluidic platform" Lab Chip 15, 3076-3085 (2015).

(Continued)

Primary Examiner — Titilayo Moloye
(74) Attorney, Agent, or Firm — Ballard Spahr LLP

(57) ABSTRACT

The present invention relates to a microtissue compartment device, comprising a compartment structure (1) having an upper surface (2) and a lower surface (3) essentially coplanar thereto, and at least two wells (4) suitable for accommodating one or more microtissues (5) in a liquid volume, each well having a lower section (4a) with a given diameter, coaxially oriented thereto an upper section (4b) with an extended diameter, and at least one conduit (6) fluidically connecting at least two wells to one another, and at least one space (13) arranged above a well. At least one well has, in its upper section, a relief structure (9) that prevents spreading or overflow of a liquid volume comprised in said well into space (13).

20 Claims, 11 Drawing Sheets

(56) References Cited

OTHER PUBLICATIONS

Figure 1A:
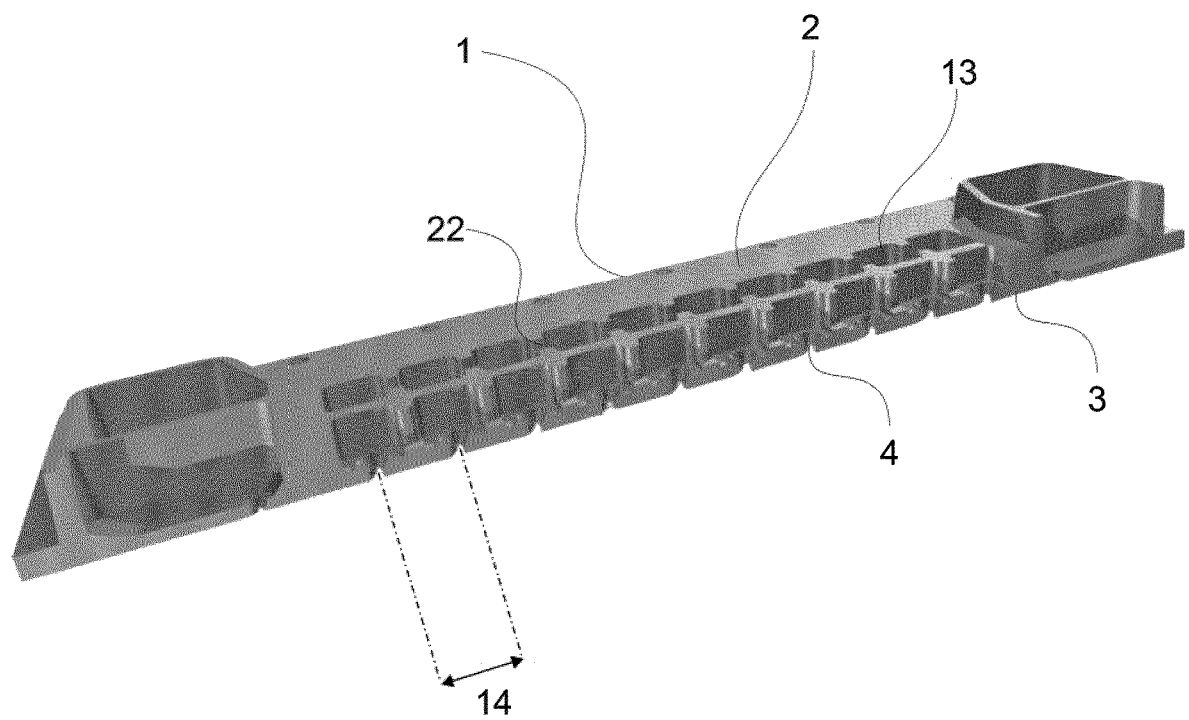

Torisawa, Y. et al. "A multicellular spheroid array to realize spheroid formation, culture, and viability assay on a chip", Biomaterials 28, 559-566 (2007).
Wu, L. et al. "Microfluidic self-assembly of tumor spheroids for anticancer drug discovery", Biomed. Microdevices 10, 197-202 (2008).
International Search Report and Written Opinion were dated Dec. 4, 2018 by the International Searching Authority for International Application No. PCT/EP2018/068553, filed on Jul. 9, 2018 and published as WO 2019/008189 on Jan. 10, 2019 (Applicant—INSPHERO AG, et al.)(9 Pages).
PCT, PCT/EP2018/068553 (WO 2019/008189), Jul. 9, 2018 (Jan. 10, 2019), INSPHERO AG.

\* cited by examiner

A

B

MICROTISSUE COMPARTMENT DEVICE

CROSS-REFERENCE TO RELATED PATENT APPLICATIONS

This application is a U.S. national phase application of International Application No. PCT/EP2018/068553, filed Jul. 9, 2018, and claims the benefit of priority to GB Application No. 1710955.4, filed on Jul. 7, 2017. The content of these earlier filed applications is hereby incorporated by reference herein in its entirety.

FIELD OF THE INVENTION

The present invention relates to the field of 3D tissue cultures and its applications in drug testing.

INTRODUCTION 3D tissue cultures are more and more used in the testing or screening of compounds for their toxicity, immunogenity or therapeutic effect. In one specific embodiment, an array of different or similar 3D tissue cultures connected to one another is exposed to the same test compound, to (i) investigate the different effects the compound has on one of the different tissues and (ii) be able to consider potential communication or cross talk between the different tissues in response to such exposure.

These devices are sometimes called "organ-on-a-chip", or even "organism-on-a-chip" or "body-on-a-chip". More recently they are summarized as "microphysiological systems". Microphysiological systems combine microfluidic technology and cell/tissue culturing and are capable of emulating human (or any other animal species') biology in vitro at the smallest biologically acceptable scale, defined by purpose.

There are many devices and methods published according to which, for example, microtissue spheroids can be formed inside a chip and cultured there under flow over time. See Ruppen et al. (2015), Occhetta et al. (2015), Kwapiszewska et al. (2014), Jin et al. (2011), Hsiao et al. (2009), Torisawa et al. (2007) or Wu et al 2008).

Only a few exist, however, in which microtissue spheroids are formed externally by using dedicated platforms and only then transferred and loaded into a microfluidic culturing chip.

In these embodiments, microtissue spheroids are either pipetted into large—large in relation to the size of the microtissue—reservoirs (also called trans-wells, Maschmeyer et al. 2015) or trapped using specially designed microfluidic structures (Ruppen et al. 2014).

For the first, the reservoirs have relatively large volumes and there is the risk that spheroids merge, if they touch each other forming larger tissue clumps over time. The second is rather cumbersome, depends on flow and is difficult to apply for routine use. Unloading of spheroids is difficult, when not impossible without their destruction.

Kim et al (2015, 2016) disclose a loading channel perpendicular to the microfluidic channel through which the microtissue is guided into the microcompartment. In this device, the platform has to be tilted to forward the spheroid into the compartment, where it sits non-immobilized. Over time, the spheroid can escape back into the loading channel during culturing, the loading channel constitutes a relatively large dead volume, and spheroids are not directly accessible and therefore difficult to unload. The loading channel in closed by a pin inserted into the loading port. This is a manual, not automatable process prone to introduce bubbles into the system, displace the microtissue spheroid due to a pump effect during introduction and bears a risk of leaking due to a not fully tight fitting.

The same considerations apply to organoids, which are miniaturized and simplified versions of organs produced in vitro, and which are meant to mimic the micro-anatomy of an organ, and precision cut tissue slices, which are viable ex vivo explants of tissue with a reproducible, well defined thickness, as well as to 3D tissue spheroids, embryoid bodies and islets.

For this reason, microtissue spheroids, organoids precision cut tissue slices, 3D tissue spheroids, embryoid bodies and islets will be referred to as "microtissues" hereinafter. All disclosures and conclusions made herein with regard to microtissue spheroids do apply to organoids and precision cut tissue slices as well.

SUMMARY OF THE INVENTION

It is one object of the present invention to provide a device that allows the synchronous cultivation of two or more microtissues and the synchronous exposure to thereof to one or more test compounds, which device allows simple and error-free and automation-compatible deposition of microtissues in the respective culture wells, and removal thereof for downstream analysis.

It is another object of the present invention to provide a device that allows to culture microtissues in microtissue compartments under continuous or varying and uni-directional or bi-directional flow conditions between two or more microtissue compartments.

It is another object of the present invention to provide a device that allows the synchronous cultivation of two or more microtissues and the synchronous exposure to thereof to one or more test compounds, which device can be prefabricated, and preloaded with suitable microtissues, prior to shipping the device to a third party.

These and further objects are achieved by the subject matter of the independent claims, while the dependent claims as well as the specification disclose further preferred embodiments.

EMBODIMENTS OF THE INVENTION

Before the invention is described in detail, it is to be understood that this invention is not limited to the particular component parts or structural features of the devices or compositions described or process steps of the methods described as such devices and methods may vary. It is also to be understood that the terminology used herein is for purposes of describing particular embodiments only, and is not intended to be limiting. The mere fact that certain measures are recited in mutually different dependent claims does not indicate that a combination of these measures cannot be used to advantage. Any reference signs in the claims should not be construed as limiting the scope. It must be noted that, as used in the specification and the appended claims, the singular forms "a," "an" and "the" include singular and/or plural referents unless the context clearly dictates otherwise. Further, in the claims, the word "comprising" does not exclude other elements or steps. The mere fact that certain measures are recited in mutually different dependent claims does not indicate that a combination of these measures cannot be used to advantage.

It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure, and avoid lengthy repetitions.

According to one embodiment of the invention, a microtissue compartment device is provided, comprising a compartment structure having
  (i) an upper surface and a lower surface essentially coplanar thereto, and
  (ii) at least two wells suitable for accommodating one or more microtissues in a liquid volume, each well having
    a) a lower section with a given diameter,
    b) coaxially oriented thereto an upper section with an extended diameter, and
  (iii) at least one conduit fluidically connecting at least two wells to one another, and
  (iv) at least one space arranged above a well.

At least one well has, in its upper section, a relief structure that prevents spreading or overflow of a liquid volume comprised in said well into said space above the well.

The upper section may preferably adopt a funnel-like shape, while the lower section 4a may preferably have a circular or oval cross section.

Such relief structure can either comprise a non-wettable area (i.e., comprising a hydrophobic area, or an area equipped with lotus effect), or an overflow-preventing edge. Overflow is prevented through surface tension or capillary pinning of the liquid and coherent forces between the liquid and the surface of the relief structure.

The extended diameter of the upper section of the well serves as a loading port through which a microtissue can be dispended or transferred into the well by means of a suitable pipette, a pipette array, or a pipetting robot.

According to one embodiment of the invention, the device further comprises at least one conduit connecting at least one space above a well to either another space above a neighboring well or to the exterior. These conduits serve to allow gaseous medium to circulate between the different wells, and allow pressure equilibration between the different spaces above the wells.

According to one embodiment, the spheroid is loaded into a pipette tip and left to settle down to the pipette tip by gravity. The tip is then placed into the funnel. The liquid in the pipet tip and the liquid in the chamber merge and the spheroid just drops down into the chamber only by gravity.

The funnel-like shape helps reliable positioning and centering of the pipette tip with respect to the lower section. This facilitates manual pipetting as well as the use of a pipette array, or a pipetting robot. The microtissue is initially picked up into a pipette tip. For transfer the pipette tip containing the "microtissue" is placed vertically inside the funnel so that the liquid in the pipette tip and the liquid in the funnel are merging. The microtissue sediments by gravity and drops from the pipette tip into the microtissue compartment or is actively pipetted into the microtissue compartment This allows microtissue transfer without liquid transfer, and further helps to minimize carry-over, reduce stress to the transferred microtissues, avoid influence on neighboring microtissues, and allows independent and parallel microtissue loading.

This process is even more facilitated when the upper section of the well and/or the lower section of the wells and/or the space above the well are arranged coaxially.

The space above the well is defined by a compartment. Such a compartment above a well has a circumferential wall. In typical embodiments there are openings between portions of this circumferential wall between neighboring compartments. In some embodiments the circumferential wall has a lower portion that defines a contiguous circumferential inner surface. In such embodiments an upper portion of the circumferential wall may contain openings between of the circumferential walls of neighboring compartments as shown in FIG. 1A.

As will be described below, the loading port can optionally be closed seamlessly using a specifically fitting plug on the upper section or left open and covered at appropriate distance so that the liquid-air interface delimits the volume of the well.

The term "microtissues" as used herein, is meant to encompass 3D cell culture models, including organoids, 3D tissue spheroids, embryoid bodies, islets, precision cut tissue slides, and the like. The microtissues can be of natural origin, or can be engineered or passively or actively reassembled from isolated cells.

This configuration has a couple of advantages over devices from the prior art (Kim et al. 2015) which provide a large, funnel-like loading port which connects to an L-shaped loading channel that eventually leads into the microtissue compartment:

(i) The deposition of the microtissues in the wells is simple and robust, by direct deposition with a pipette vertically approached from the top, and needs no further steps, like tilting or repositioning of the microtissue. The microtissue automatically falls to its correct location in the well. For microtissue loading, the device according to Kim et al. 2015 needs to be tilted so that gravity transfers the microtissue through the loading channel in its compartment, bearing the risk of jamming and/or spilling. Further, this process is time consuming and not directly compatible for automation systems and difficult to parallelize.

(ii) The deposition of the microtissue is gravity-driven and needs no application of liquid flow, so that media transfer from the pipette to the device is minimal, minimizing cross-contamination and minimizing flow in neighboring compartments, eventually detrimental to the microtissues.

(iii) The device can easily be placed onto the stage of a microscope for microtissue inspection, because a clear optical path is provided along the vertical axis of the wells.

(iv) The device has a minimized dead volume, hence ensuring that test liquids applied can be exchanged rapidly, wash out is efficient, liquids applied are not diluted, and/or exposure of microtissues thereto would be delayed, or hampered, or affected by artifacts.

(v) The liquid-air interface defines the upper boundary of the "microtissue" compartment making the compartment directly accessible with a pipette and has a "self-sealing" mechanism as soon as the pipette is again removed and the liquid-air interface re-established. No addition mechanic cover or plug is needed, which is usually required in all prior-art systems of similar kind.

(v) The open top configuration allows direct and local oxygen exchange and avoids the trapping or development of gas bubbles interfering with microtissue cultures and liquid flow. In contrast thereto, the configuration according to Kim et al. 2015 bears the risk of trapping air bubbles, and furthermore restricts oxygen exchange in the compartment.

(vi) The open top configuration further allows simple removal of a microtissue, by aspirating it into a pipet tip (1-20 µL volume removal depending on design).

In one embodiment, the device further comprises a base structure having an upper surface and a lower surface essentially coplanar thereto, which base structure is releasably or irreleasibly attached to the lower surface of the compartment structure.

In this embodiment, the microtissue compartment device comprises essentially two parts, namely the compartment structure and the base structure. The base structure forms the bottom of the wells of the compartment structure, i.e., the wells formed in the microtissue compartment are open ended and have no bottom per se.

Such two-part structure can be produced, e.g., by die-casting, molding, embossing or 3D printing methods of suitable material, e.g., thermoplasts including polystyrene, Cyclic Olefin Copolymers (COC), Cyclic Olefin Polymers (COP), etc.

Generally, the device can also be a one part structure, i.e., without a separate base structure. Such one-part structure can e.g. be produced by 3D printing.

In one embodiment of the device according to the invention, at least one conduit is either provided in the compartment structure or in the optional base structure.

Preferably, at least one conduit consists, essentially, of a longitudinal furrow defined by two lateral walls.

In the first embodiment having the conduits arranged in the compartment structure, the conduits are arranged on the lower surface of the compartment structure, with the base structure merely forming the bottom of the conduits.

In the second embodiment having the conduits arranged in the base structure, the conduits are arranged on the upper surface of the base structure, with the lower surface of the compartment structure forming the ceiling of the conduits, when the two are attached to one another.

In one embodiment of the device according to the invention, the upper section of at least one well is essentially funnel-shaped, with the diameter thereof extending in an upward direction.

This arrangement facilitates loading of the wells, which can be achieved in a very simple way by using the funnel structure: The spheroid is loaded into a pipette tip and left to settle down to the pipette tip by gravity. The tip is then placed into the funnel. The liquid in the pipet tip and the liquid in the chamber merge and the spheroid just drops down into the chamber only by gravity.

The funnel helps positioning of the pipette tip, as it provides a self-centering structure. This facilitates manual pipetting as well as the use of a pipette array, or a pipetting robot.

In one embodiment of the device according to the invention, at least one well has an essentially elliptic or circular cross section.

Both embodiments allow that a curved liquid-air interface or droplet forms at the top of the well, at the border to the compartments 13 above the wells, as a result of pressure equilibration between liquid and the gaseous medium in the compartments 13 above the wells. Said gaseous medium is, e.g., air, oxygen, or $CO_2$ enriched air. Herein, said gaseous medium will simply referred to as "air". The curved area increases the size of the liquid-air interface, and hence improves the gas exchange between the culture liquid and the surrounding gaseous medium.

In one other embodiment of the device according to the invention, the bottom structure of at least one well—either arranged in the compartment structure or in the base structure—has an elliptic or circular pit arranged concentrically to the well or arranged within the well.

Said pit serves to accommodate the lower part of the microtissue, hence centering the latter. In such way, microscopic investigations are facilitated and the exposure to the liquid medium is made more reproducible.

In one other embodiment of the device according to the invention at least one well has at least one lip structure, extending downward from the lower surface of the compartment structure, which lip structure protrudes into the conduit and in such way deflecting liquid flowing through the conduit to enter the well from a direction that deviates from the direction determined by the longitudinal axis of the conduit. In such way, it is avoided that liquid flow directly hits the microtissues, which could expose it to too high shear forces and/or lead to a dislocation thereof, and hence hamper any measurements, or the reproducibility of the exposure to the test agents comprised in the liquid.

In one other embodiment of the device according to the invention the compartment structure or the base structure comprises at least one reservoir fluidically connecting to at least one well by means of a conduit.

Similar to the conduits connecting the wells, said conduit can either be in the compartment structure or in the base structure, where it may consist, essentially, of a longitudinal furrow defined by two lateral walls, and a bottom or ceiling.

In said reservoir different types of liquid media can be provided:
a) Culture media for culturing the microtissues
b) Washing media for washing the microtissues, or washing out other media from the entire system
c) Test media comprising one or more test compounds to which the microtissues are exposed By leaving the reservoir uncovered, medium can be sampled at every desired time point for analysis. Optionally, the said reservoir can be reversibly closed with a sealing structure or cover, to avoid contamination or spilling of liquid. In such case, the respective sealing may optionally be made in such way that it can be punched through with the pipette tip, so that is does not have to taken off for sampling.

The perfusion of the entire system, i.e., the transport of media from the at least one reservoir through at least one of the wells to a second reservoir, can be pump-free. The wells have an open top configuration. Therefore, the entire device may be placed on a tilting device (sometimes called "rocker"), so that, by tilting the device periodically or permanently, liquid is transported through the conduits following the direction of gravity.

The perfusion of the system can be accomplished by means of an external pump connected to the at least one of the conduits.

As discussed elsewhere, the device according to the invention provides the possibility to build up liquid-air interfaces at the said relief structures of the wells. The surface tension of the liquid provides a pressure barrier preventing liquid from spreading into the upper space and preserving the function of the well as a liquid compartment.

Because of the and hydrostatic pressure in a rocker-based perfusion setup, the drops which occur in the lowermost wells will swell, while the drops in the uppermost wells will shrink. Hence, with each tilting of the platform, an additional miniature pumping effect will occur in the microtissue compartment, that supports the exposure of the microtissues to the media and efficient media exchange of the dead volume in the compartment, which effect does not occur in a device according to the art, where no such liquid-air interfaces exist.

Preferably, at least one well has a diameter of between ≤3 mm and ≥0.3 mm, with 0.4; 0.5; 0.6; 0.7; 0.8; 0.9; 1; 1.1; 1.2; 1.3; 1.4; 1.5; 1.6; 1.7; 1.8; 1.9; 2; 2.1; 2.2; 2.3; 2.4; 2.5; 2.6; 2.7; 2.8 or 2.9 mm as preferred diameters.

In a preferred embodiment, the height of the conduit is smaller than the diameter of the microtissue comprised in the well, so as to avoid that the microtissues are washed out of their wells. Artificial microtissues typically have diameters between 100 μm and 500 μm.

Preferably, at least one conduit has a height of between ≤1 mm and ≥0.03 mm, with 0.06; 0.09; 0.12; 0.15; 0.18; 0.21; 0.24; 0.27; 0.3; 0.33; 0.36; 0.39; 0.42; 0.45; 0.48; 0.51; 0.54; 0.57; 0.6; 0.63; 0.66; 0.69; 0.72; 0.75; 0.78; 0.81; 0.84; 0.87; 0.9; 0.93; 0.96; or 0.99 as preferred heights.

The height of the conduit is for example determined by the height of the lateral walls of the furrows comprised in the compartment structure or the base structure.

In one other embodiment of the device according to the invention, the device comprises at least one row of 3 or more wells, being spaced apart from one another in a grid spacing pattern of 9 mm, 4.5 mm or 2.25 mm.

The term "being spaced apart from one another in a grid spacing pattern of X mm" determines the distances between the centers of the wells involved.

This follows the standardized dimensions of microtiter plates as determined by ANSI standard ANSI SLAS 4-2004 (R2012) (formerly recognized as ANSI/SBS 4-2004)

| Plate type | grid spacing pattern |
| --- | --- |
| 96 | 9 mm |
| 384 | 4.5 mm |
| 1536 | 2.25 mm |

In one other embodiment of the device according to the invention, the device further comprises one or more sealing structures for sealing the wells from their upper side of the compartment structure.

The sealing protects the microtissues, avoids contamination, avoids or reduces evaporation of liquid. Such sealing structures further facilitate the shipping of preloaded or empty microtissue compartment devices, in that they avoid contamination thereof, or loss of liquid or microtissues.

Preferably, the sealing structure is at least one selected from the group consisting of:
 a plug inserted into the space above the wells, and/or
 a sealing film attached to the upper surface of the compartment structure.

It is important to understand that both embodiments make sense both in an empty microtissue compartment device, as well as in a microtissue compartment device that is preloaded with a liquid, optionally preloaded with microtissues.

A sealing film merely avoids evaporation of liquid and contamination of the wells, or their content. Still, in such embodiment, a liquid-air interface can be maintained, to ensure gas exchange between the liquid phase and the surrounding gaseous medium, hence ensuring, e.g., sufficient oxygen supply for the microtissues. Further, there is no contact between sealing structure and liquid. Preferably, said sealing film is made from a gas permeable membrane, e.g., from silicone.

In addition thereto, a plug, if inserted deeply into the space above the wells, can furthermore effectively seal the wells, so as to avoid spilling of liquid. To still yield sufficient oxygen supply, such plug can comprise a gas permeable membrane, e.g., from silicone.

Preferably, said plug is designed to minimally displace the liquid in the well, either through too deep insertion into the well or by compression of gaseous medium in the space above the wells.

Preferably, the sealing film or plug is transparent, so as to allow light passing through. In such case, the microtissues can easily be inspected optically with the sealing film or plug in place, and can even be inspected microscopically, e.g., on an inverted microscope.

Preferably, the sealing film or plug is made in such way that it can be punched through with the pipette tip, so that is does not have to taken off for microtissue loading, or removal at the end of an experiment.

The sealing film can for example be made of a non-woven Rayon material, as e.g., provided by Sigma Aldrich under the brand name Breathe-Easier, or from Polyurethane, as e.g., provided by Sigma Aldrich under the brand name Breathe-Easy.

According to one other aspect of the invention, a strip is provided, which strip is suitable for disposing in a frame structure that is compatible to the microtiter plate standard. The strip accommodates at least one microtissue compartment device or compartment structure according to the above description.

According to one other aspect of the invention, a frame structure compatible to the microtiter plate standard is provided, said frame structure comprising at least one strip or at least one microtissue compartment device or compartment structure according to the above description.

Hence, multiple of strips, or compartment structures, comprising wells and reservoirs can be aligned side by side in the frame structure, to execute experiments in parallel, i,e, with different test agents or different concentrations of the same test agent.

The term "frame structure compatible to the microtiter plate standard" determines that such frame follows the rules set forth in ANSI standard SLAS 1-2004 (R2012) (formerly recognized as ANSI/SBS 1-2004).

According to one other aspect of the invention, a model organism on a chip is provided, said model organism comprising at least one microtissue compartment device or compartment structure, or at least one strip, or at least one frame structure, according to the above description, with two or more different microtissues arranged in the wells of the compartment device.

In such device, different types (liver, heart, tumor, brain, etc.) of microtissues are combined in different wells for multi-tissue configurations. All wells are connected to one another by the conduits discussed herein, and are hence exposed to the same type of liquids. Hence, the effect of a given test composition on different tissue or organ models can be tested, and the crosstalk between the different tissue or organ models can be considered if necessary.

In this embodiment, the combination of multiple wells allows to create physiological-near condition, which reflect the quantitative relationship of different tissues of a test organism. For example, in humans the volume ratio of liver:heart is 6:1. To account for this quantitative relationship, devices from the prior art (U.S. Pat. Nos. 7,288,405, 8,748,180) provide a liver compartment which is 6 times larger than the heart compartment, both connected via microchannels.

The present device offers much more flexibility, in that, to e.g. reflect the quantitative relationship discussed above, 6 wells can be loaded with a liver microtissue, and 1 well can be loaded with a heart microtissue. In order to reflect the quantitative relationships of other organ pairs, the loading of the wells can be changed accordingly.

In one embodiment, such model organism on a chip can be prefabricated and then shipped to end users ready for use.

According to one other aspect of the invention, a method of testing one or more test compounds on potential physiological or toxic effects on a physiologic system is provided, said method comprising
 a) providing at least one microtissue compartment device or compartment structure, or at least one strip, or at least one frame structure, or at least one model organism on a chip according to the above description,
 b) (optionally) loading one or more microtissues into the wells provided by said microtissue compartment device or compartment structure, strip or frame structure,
 c) loading a liquid medium into at least one of the reservoirs provided in the microtissue compartment device or compartment structure, which liquid medium comprises at least one test compound, perfusing the wells with the liquid medium, and
 d) monitoring or analyzing at least one of the microtissues and/or sampling and analyzing the liquid medium.

In one embodiment, the growth and/or the viability of at least one of the microtissues is monitored ort analyzed when the latter is still in the device.

In this embodiment microtissues can be monitored or analyzed during or after exposure to the at least one test compound.

The proliferation and growth rate of tumor microtissues can for example be analyzed by using brightfield microscopy on an inverted microscope, preferably when the microtissues are still in the well. Tumor cells expressing fluorescent markers can are analyzed using fluorescence microscopy. Further, in this embodiment the mictotissues are amendable for high-throughput, high-content scanning analysis systems, including Celligo, Cell3imager, etc.

Liver microtissues can be analyzed upon their morphology, where compact microtissues indicated good viability, whereas dead cells tend to leave the microtissue, or the microtissue disintegrates. This can be done, preferably when the microtissues are still in the well.

Microtissues can also be stained in the wells by using, e.g. life/dead staining, and subsequent analysis on an inverted fluorescence microscope. An example for such life/dead staining assay is the CellTiter-Blue Cell Viability Assay by Promega. Further examples for such approach are e.g. shown in Kijanska and Kelm, 2016.

In one other embodiment, at least one of the microtissues is removed from the device for analysis. In such case, microtissues can be stained with different dyes and analyzed using bright field microscopy, or fluorescence microscopy, or confocal microscopy, or light sheet microscopy.

The microtissues can also be analyzed using lytic viability assays, like e.g. the CellTiter-Glo 3D Cell Viability Assay. The microtissues can be analyzed using histology and respective staining.

The media can be sampled during the experiment or at the end and analyzed after sampling. In such analysis, different markers, metabolites, hormones or second messengers, or cytokines may be of interest, e.g.:

The abundance of specific viability markers such as albumin is a marker of well-functioning liver cells Human albumin can be quantified with, e.g., the Human Albumin ELISA Quantitation Set, E80-129, by Bethyl.

The amount of Insulin secretion is a marker for the viability of pancreatic islets, and can be determined with, e.g., STELLUX® Chemi Human Insulin ELISA, 80-IN-SHU-CH01, ALPCO, USA Further the medium can be analyzed upon how a compound concentration changes over time that had been added initially.

EXPERIMENTS AND FIGURES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Example 1

8 liver microtissues and 2 tumor microtissues are incubated with one or more tumor-specific prodrugs. Liver microtissues can e.g. be produced as disclosed in WO2015158777A1. Tumor microtissues can e.g. be produced as disclosed in Kelm et al., 2003

In this case, the reason for the specific quantitative selection is that 8 liver microtissues are used to have a maximum number of cells for metabolizing the prodrug, and two tumor microtissues just to have 2 replicates for the observed effects.

In other embodiments the selection of the quantitative ratio can be done to reflect the quantitative ratio of tissues in the human body, e.g., (liver:heart) or (liver:hepatocarcinoma).

A prodrug is a compound that first needs to be activated through liver-metabolic conversion into an active, tumor-specific agent. The efficacy and toxicity of the one or more prodrugs after bioactivation can be both investigated simultaneously using the present two-tissue model.

A device is prepared according to FIGS. 7A/7B, i.e., 12 strips with 10 wells each. 8 wells of each strip are loaded with liver microtissues, and 2 wells of each strip are loaded with tumor microtissues.

1. Test of Different Concentrations of the Same Test Agent:

The individual steps include:
1. Loading of a common medium (e.g.: 3D InSight™ Cell-Culture Media by Insphero) into the reservoirs of the system
2. Loading of the two microtissue types in the related wells (multiple medium conditions, tissue ratios and technical replicas can be prepared)
3. Sealing of the wells by means of a sealing film
4. Set up of the systems on a programmable tilting device inside an incubator
5. Application of the compound at 12 different concentrations in the reservoirs of the 12 strips
6. Automated tilting inducing perfusion in all conditions in parallel over a defined time frame (1-30 days, for example)
7. During the experiment
   a. Monitoring tumor growths with microscopy
   b. Sampling medium at defined time points for analysis
   c. Adding/exchanging medium, if required
   d. Removing selected microtissue for analysis
8. At the end of the experiment
   a. Removing medium for analysis
   b. Removing microtissue for analysis
9. Tumor microtissues are analyzed upon the effect of the prodrug and the metabolized prodrug.
10. Liver microtissues are analyzed upon toxic effects of the prodrug and the metabolized prodrug.
11. Sampled medium is analyzed upon concentrations of the prodrug and the metabolized prodrug, giving information on the conversion efficiency and compound half-lives, and tissue-specific markers related to functionality and viability.

2. Test of Different Test Agents:

The individual steps include:
1. Loading of a common medium (e.g.: 3D InSight™ Cell-Culture Media by Insphero) into the reservoirs of the system
2. Loading of the two microtissue types in the related wells (multiple medium conditions, tissue ratios and technical replicas can be prepared)
3. Sealing of the wells by means of a suitable sealing film
4. Set up of the systems on a programmable tilting device inside an incubator
5. Application of 12 different test agents in the reservoirs of the 12 strips
6. Automated tilting inducing perfusion in all conditions in parallel over a defined time frame (1-30 days, for example)
7. During the experiment
   a. Monitoring tumor growths with microscopy
   b. Sampling medium at defined time points for analysis
   c. Adding/exchanging medium, if required
   d. Removing selected microtissue for analysis
8. At the end of the experiment
   a. Removing medium for analysis
   b. Removing microtissue for analysis
9. Tumor microtissues are analyzed upon the effect of the prodrug and the metabolized prodrug.
10. Liver microtissues are analyzed upon toxic effects of the prodrug and the metabolized prodrug.
11. Sampled medium is analyzed upon concentrations of the prodrug and the metabolized prodrug, giving information on the conversion efficiency and compound half-lives, and tissue-specific markers related to functionality and viability.

FIGURES

FIG. 1A shows a microtissue compartment device, comprising a compartment structure 1 having an upper surface 2 and a lower surface 3 essentially coplanar thereto, and at least two wells 4 suitable for accommodating one or more microtissues in a liquid volume.

The device may further comprise a base structure (not shown) having an upper surface and a lower surface essentially coplanar thereto, which base structure is releasably or irreleasably attached to the lower surface of the compartment structure, and provides the bottom structures for the wells 4 in the compartment structure.

FIG. 1A further shows spaces in the form of compartments 13 above the wells 4, which comprise a gaseous medium, e.g., air, oxygen, or $CO_2$ enriched air. Herein, said gaseous medium will simply referred to as "air". As can be seen, though this is an optional feature, the compartment 13 can be arranged coaxially to its corresponding well 4.

FIG. 1A further shows optional channels 22, which may be implemented to connect the compartments above the wells, to allow gaseous medium to circulate between the different wells, and allow pressure equilibration between the different compartments above the wells.

Figure 1B:
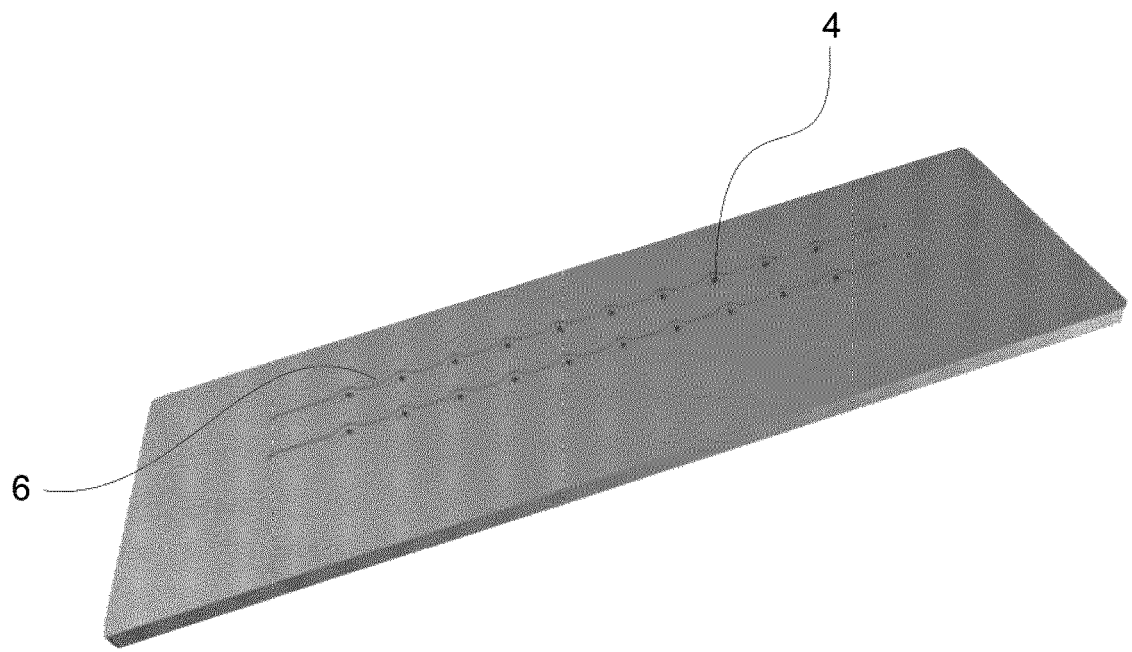

FIG. 1B shows one embodiment of the lower surface of said compartment structure, which conduits 6 connecting the wells 4.

Interestingly, the base structure discussed above can, in one embodiment, look similar to said base structure, namely in case the conduits are not provided in the lower surface of the compartment structure, but in the upper surface of the base structure.

Figure 2A:
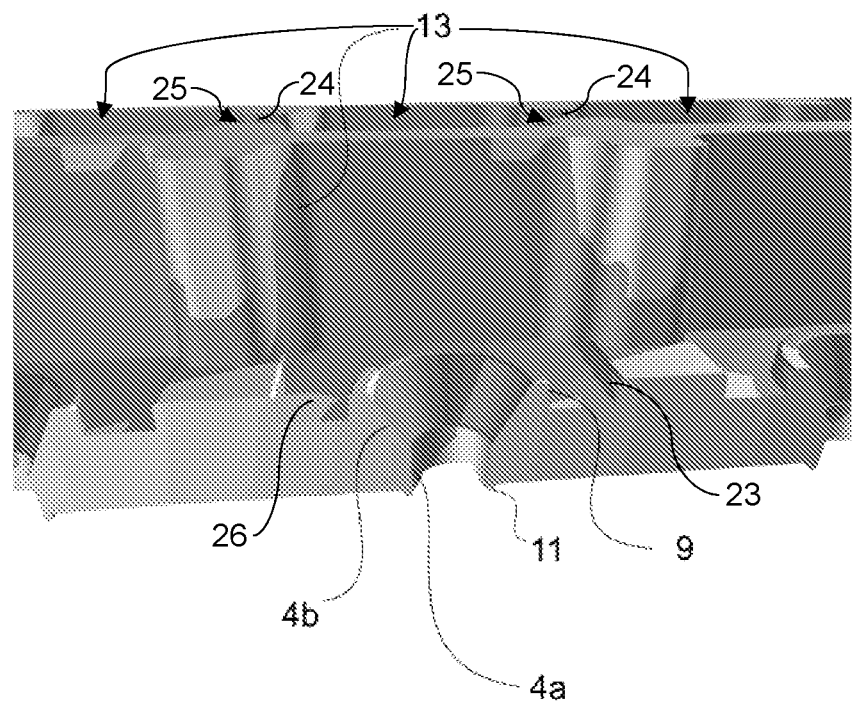

FIG. 2A shows details of the well 4 with a lower section 4a with a given diameter, and coaxially oriented thereto an upper section 4b with an extended diameter, a relief structure 9 that prevents spreading or overflow of a liquid volume comprised in said well, and a lip structure 11, extending downward from the lower surface of the compartment structure. The lip structure protrudes into the conduit and in such way deflects liquid flowing through the conduit to enter the well from a direction that deviates from the direction determined by the longitudinal axis of the conduit. FIG. 2A further shows the compartments 13 above the wells, which comprise a gaseous medium, e.g., air, oxygen, or $CO_2$ enriched air (simply referred to as "air" herein). The compartments are each defined by a respective outer wall and a lower surface 26. The outer wall can comprise a lower contiguous peripheral inner surface 23 that peripherally encloses a portion of an interior of the compartment and an upper portion 24 that contains openings 25 to neighboring compartments.

Figure 2B:
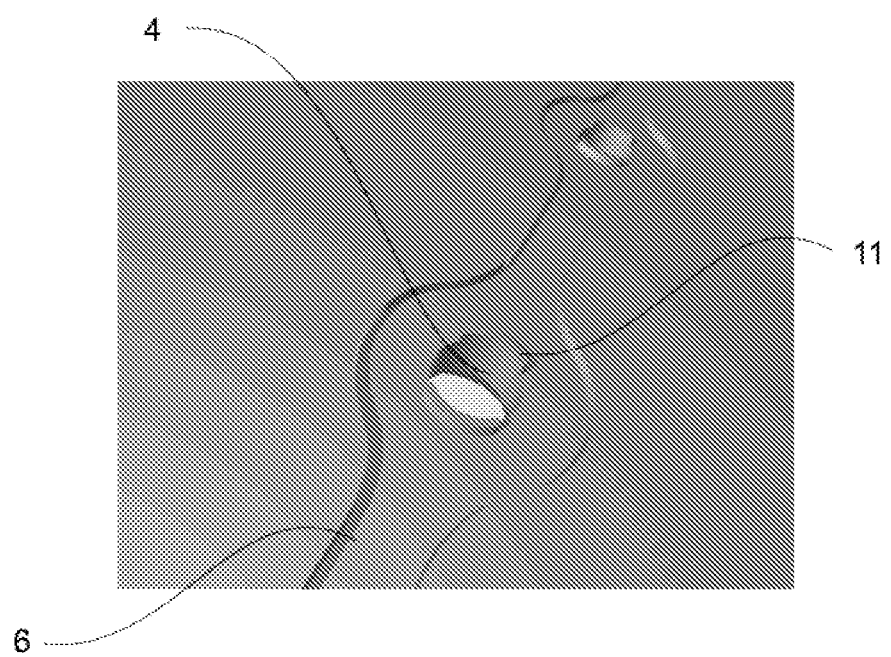

FIG. 2B shows a close up of the lower surface of the compartment structure, which conduits 6 connecting the wells 4, and the lip structure 11.

Figure 3A:
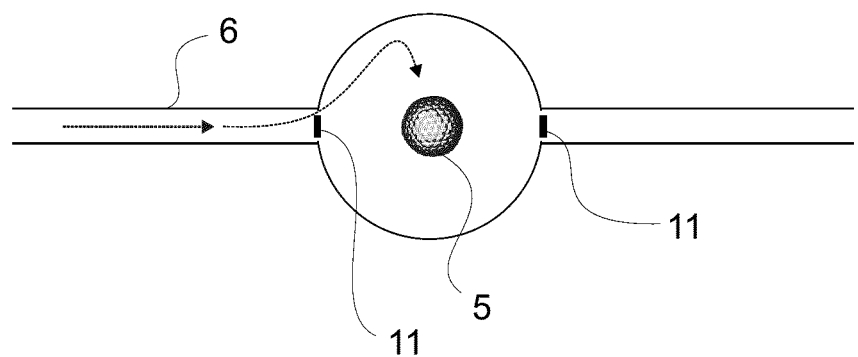
Figure 3B:
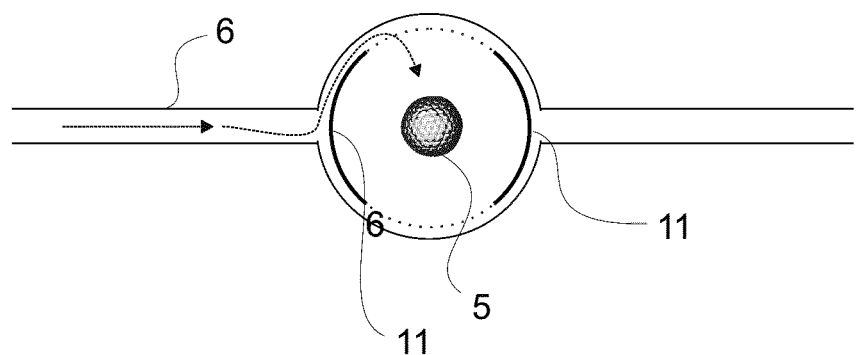

FIGS. 3A and 3B show how the lip structure 11 deflects liquid (arrow) flowing through the conduit 6 to enter the well from a direction that deviates from the direction determined by the longitudinal axis of the conduit. In such way, it is avoided that liquid flow directly hits the microtissues, which could lead to a dislocation thereof, and hence hamper any measurements, or the reproducibility of the exposure to the test agents comprised in the liquid.

Figure 4A:
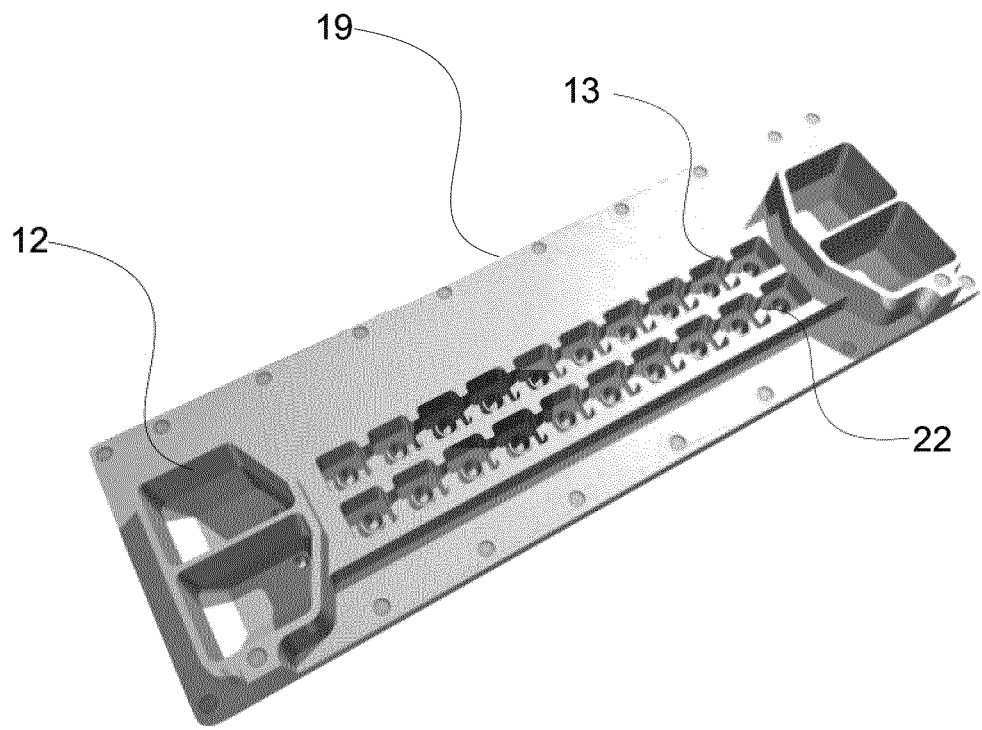

FIG. 4A shows the compartment structure from above, with reservoirs 12 fluidically connecting to at least one well 4 by means of a conduit (not shown). In said reservoir different types of liquid media can be provided:
 a) Culture media for culturing the microtissues
 b) Washing media for washing the microtissues, or washing out other media from the entire system
 c) Test media comprising one or more test compounds to which the microtissues are exposed FIG. 4A further shows the compartments 13 above the wells 4, which comprise a gaseous medium, e.g., air, oxygen, or $CO_2$ enriched air (simply referred to as "air" herein). Further, optional channels 22 are shown, which connect the compartments above the wells.

Figure 4B:
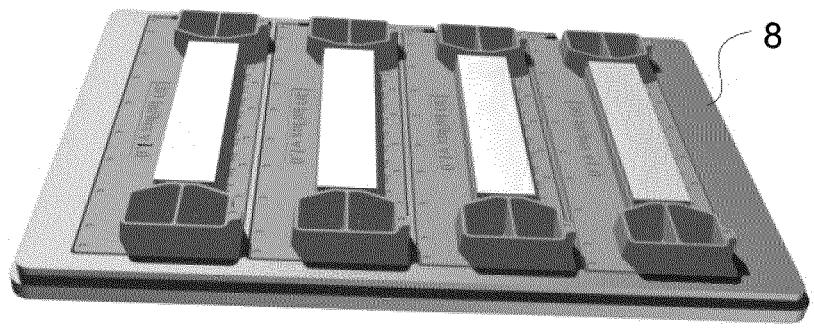

FIG. 4B shows a frame structure in which several compartment structures can be arranged.

Figure 5A:
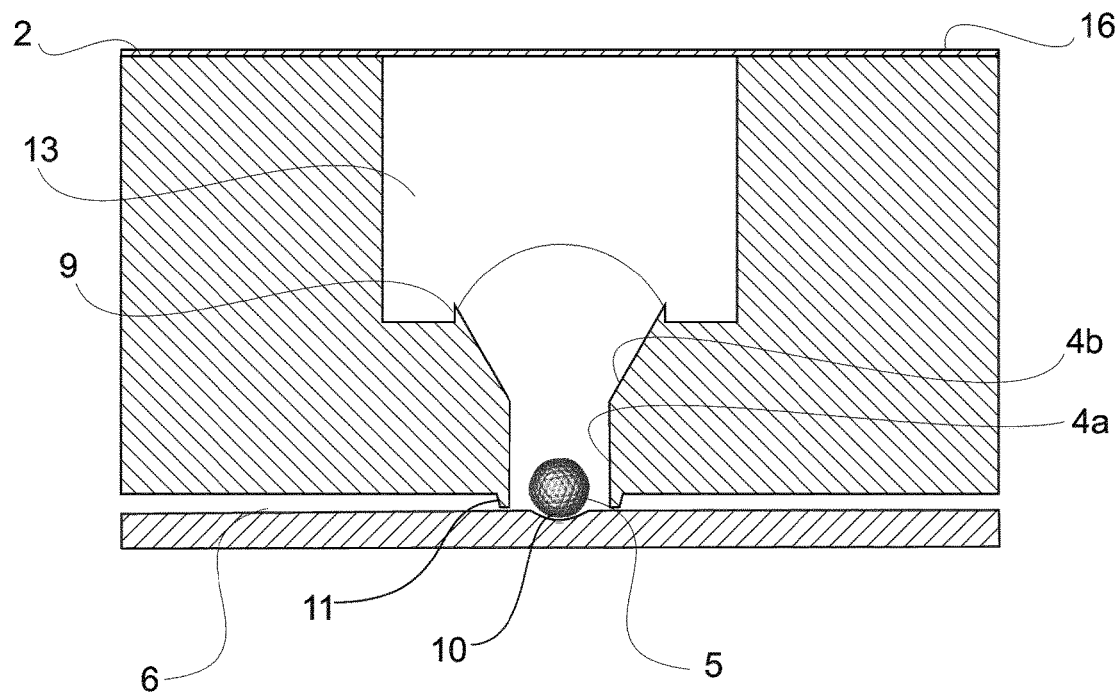
Figure 5B:
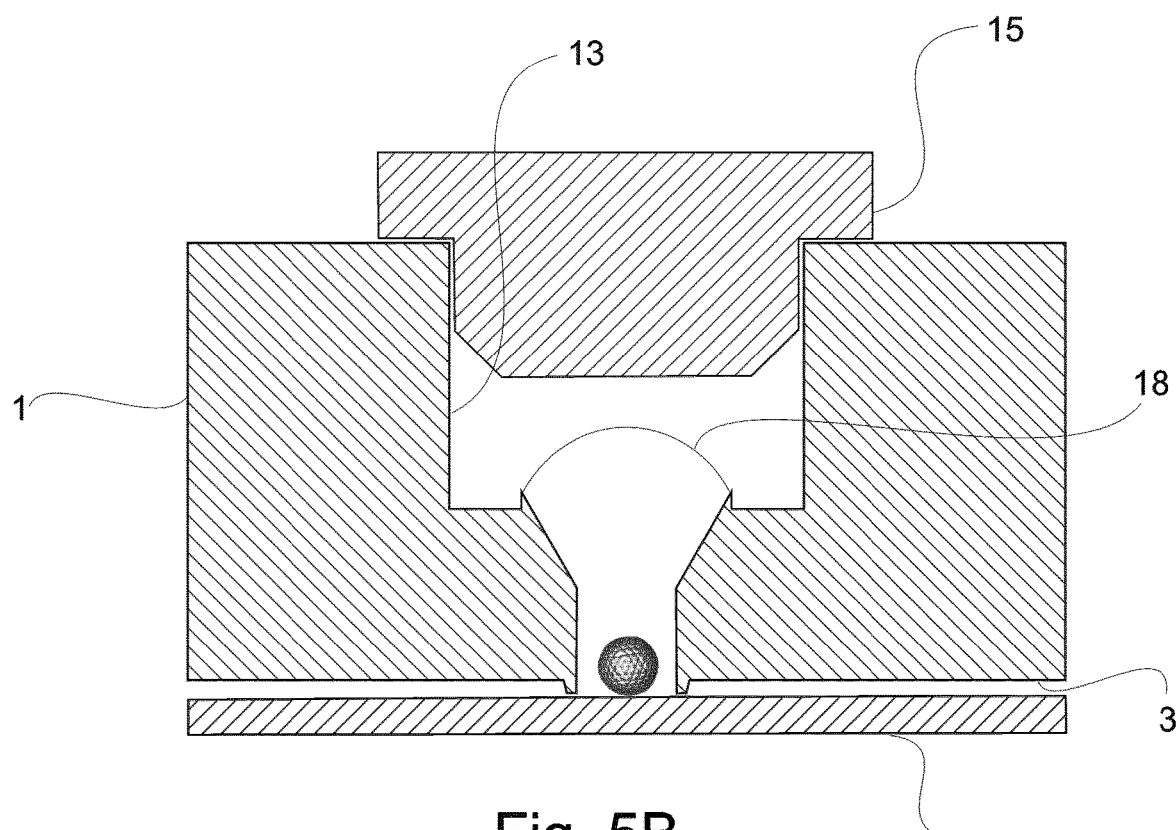
Figure 5C:
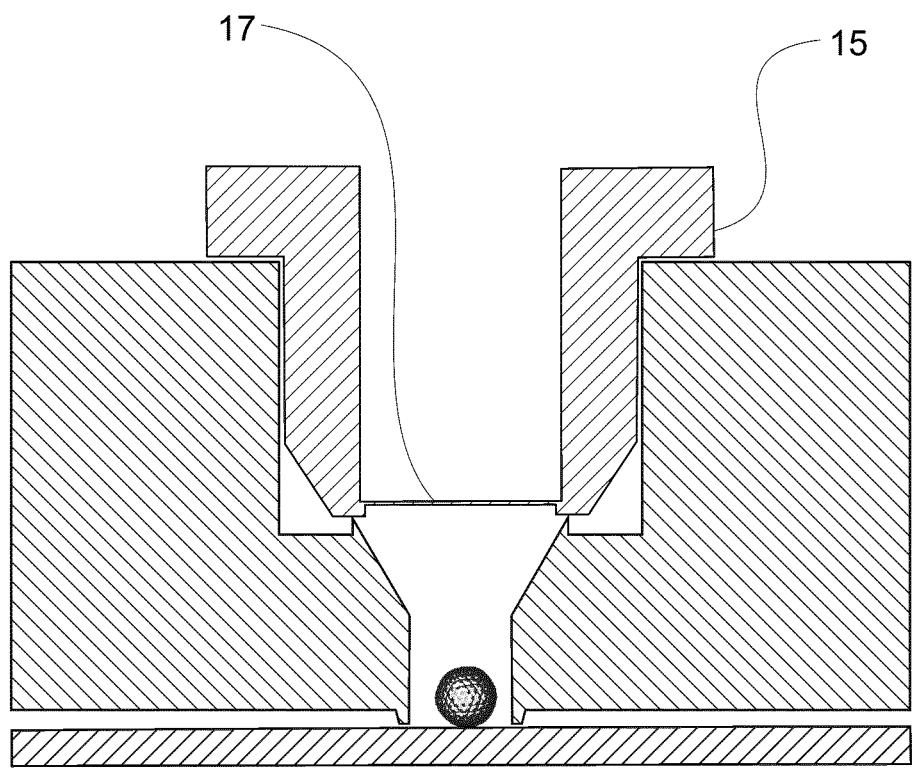

FIGS. 5A-C show cross sections of a well and its surroundings of a compartment structure, with well 4, microtissue 5, conduits 6, base structure 7, relief structure 9, and lip structure 11.

The wells have an upper section 4b, which may preferably adopt a funnel-like shape, and a lower section 4b, which may preferably have a circular or oval cross section.

Further, the compartment 13 above the wells is shown, which comprises a gaseous medium, e.g., air, oxygen, or CO, enriched air (simply referred to as "air" herein). As discussed, the conduits 6 can either be on the lower surface 3 of the compartment structure 1, or on the upper surface of the base structure 7.

Further shown are a plug 15 inserted into the compartment 13 above the wells, and, alternatively, a sealing film 16 attached to the upper surface 2 of the compartment structure 1. The sealing film merely avoids evaporation of liquid and contamination of the wells, or their content. Still, in such embodiment, a liquid-air interface can be maintained, to ensure gas exchange between the liquid phase and the surrounding air, hence ensuring sufficient oxygen supply for the microtissues. Preferably, said sealing film is made from a gas permeable membrane, e.g., from silicone.

The plug 15, f inserted deeply into the compartment 13 above the wells, can furthermore effectively seal the wells (FIG. 5C), so as to avoid spilling of liquid. To still yield sufficient oxygen supply, such plug can comprise, in one embodiment, a gas permeable membrane 17, e.g., from silicone.

In some embodiments, the base structure comprises elliptic or circular pits 10 arranged concentrically to the well, to accommodate the lower part of the microtissue 5, hence centering the latter. In such way, microscopic investigations are facilitated and the exposure to the liquid medium is made more reproducible.

The relief structure 9 is exemplarily shown in the form of an overflow-preventing edge, which allows that a droplet forms at the top of the well, by establishing a maximum contact angle, thus preventing release of the droplet by capillary pinning. This phenomenon increases the size of the liquid-air interface 18, and hence improves the gas exchange between the culture liquid and the surrounding gaseous medium.

It is to be mentioned that the relief structure can adopt different shapes, with different angles, heights, and roundings, as long as it fulfills its purpose, as described above. The relief structure can alternatively comprise a non-wettable area (i.e., comprising a hydrophobic area, or an area equipped with lotus effect), to achieve the same effect.

Further, the relief structure avoids spilling of the liquid when the device is tilted (see FIG. 9A), or when a pressure is applied in the microfluidic system, e.g., by pumping activity from the reservoirs with liquid flow through the channels. In both situations, the droplet that forms at the top of the well may increase in volume, or swell, but will not spill or overflow. In this aspect, the surface tension of liquid, which creates a pressure barrier, has a contributory effect.

Figure 6A:
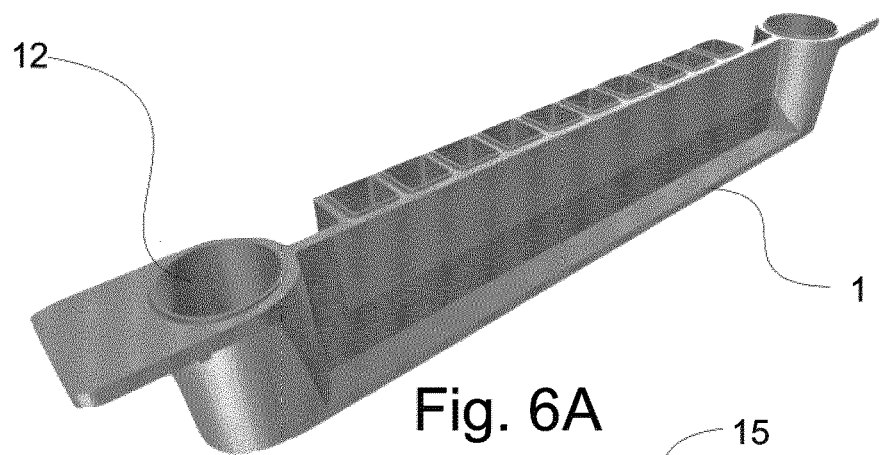
Figure 6B:
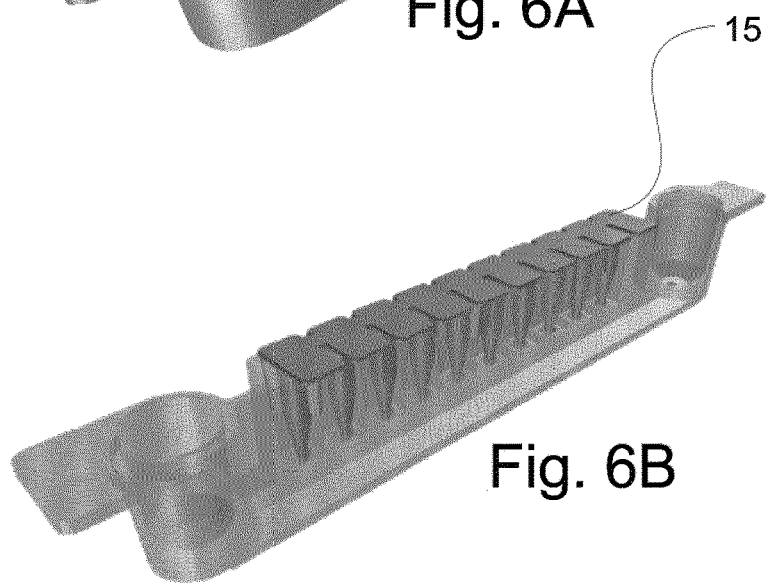
Figure 6C:
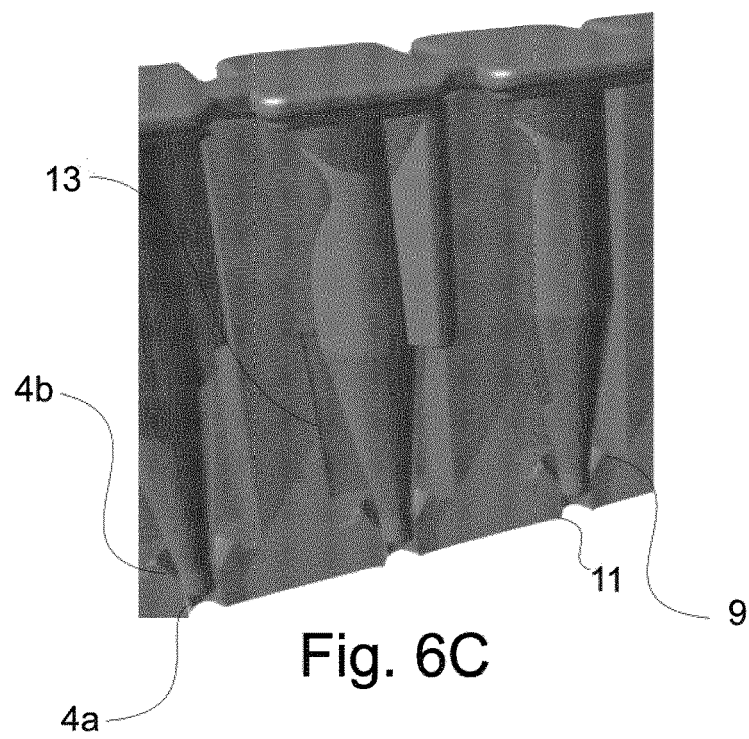

FIG. 6A-C shows an alternative embodiment of the microcompartment structure 1 with reservoir 12, plugs 15, upper sections 4b and lower sections 4a of the wells, relief structure 9 and lip stricture 11.

Figure 7:
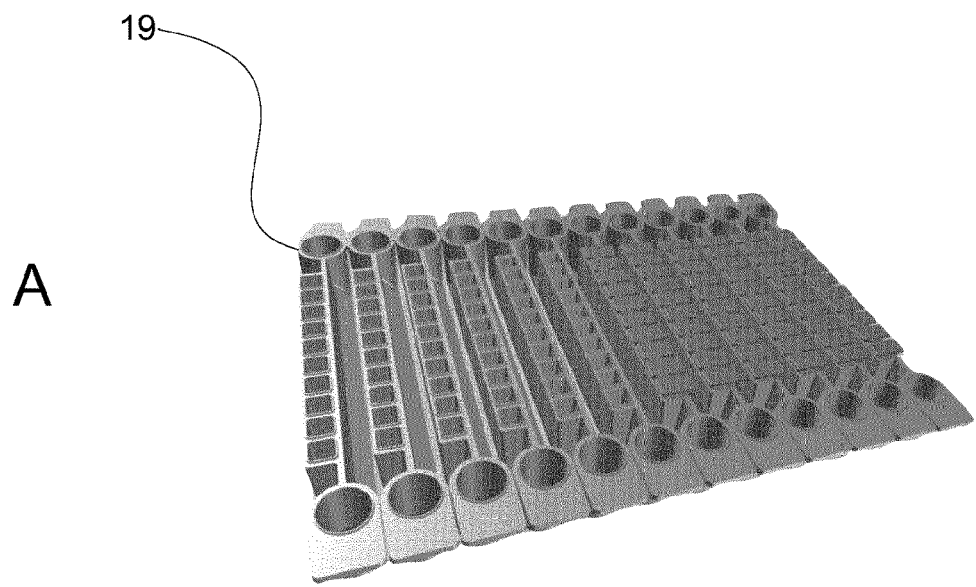
Figure 7:
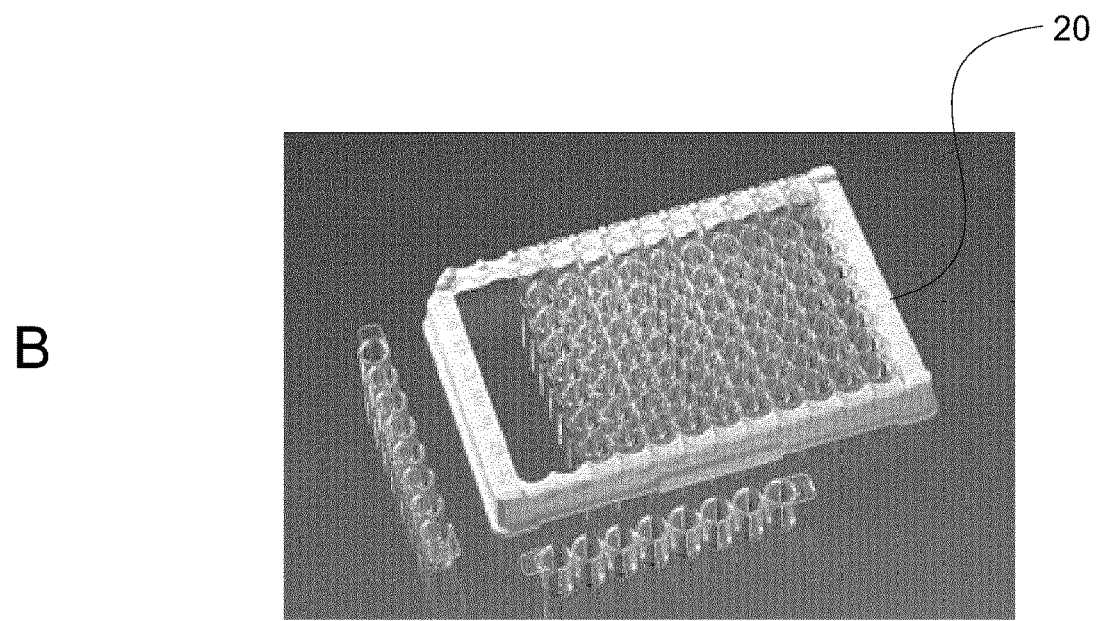

FIG. 7 shows that the microcompartment structures of FIG. 1 and FIG. 6 can adopt the form of a strip 19, which can be arranged in a frame structure 20 compatible to the microtiter plate standard.

Hence, multiple strips, or microcompartment structures, comprising wells and reservoirs can be aligned side by side in the frame structure, to execute experiments in parallel, i,e, with different test agents or different concentrations of the same test agent.

As can be seen, the strip of FIG. 7A has one row of wells. Alternatively, the strip can have more rows of wells, as, e.g., show in FIG. 4, wherein each row has its own reservoirs, and can be used with different test conditions, e.g., different test agents or different concentrations of the same test agent.

Figure 8:
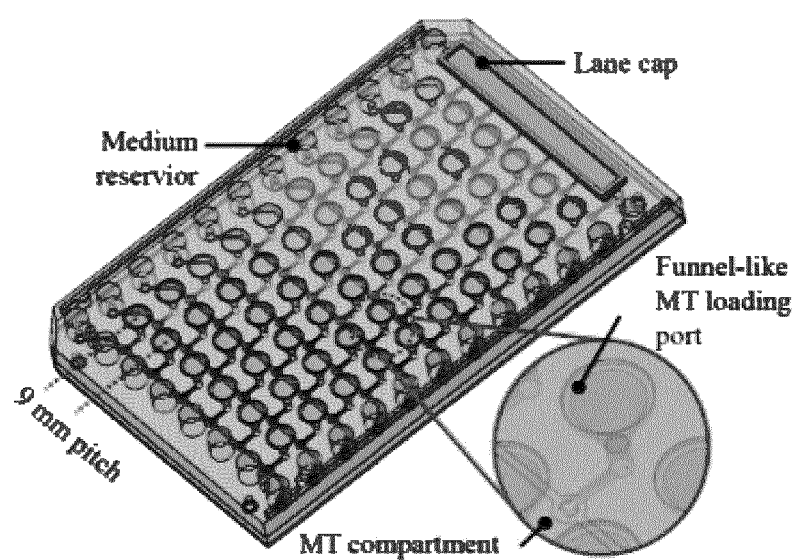

FIG. 8 shows a non-inventive embodiment form the prior art (Kim et al, 2015), which has a different layout of the wells and the loading port, making microtissue loading more difficult and error-prone.

Figure 9A:
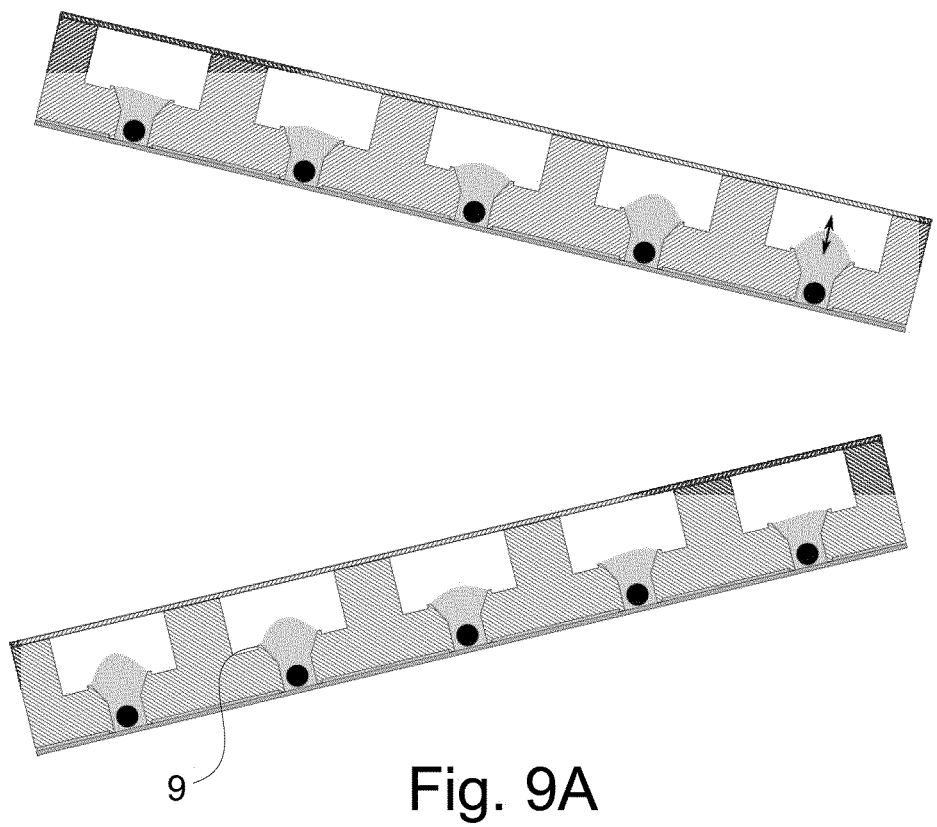

FIG. 9A shows the so-called "tilting well pump effect" caused by tilting of a device according to the invention with liquid-air interfaces. Because of the hydrostatic pressure, the drops which occur in the lowermost wells will swell, while the drops in the uppermost wells will shrink. Hence, with each tilting of the platform, and additional pumping effect will occur, which does not occur in a device according to the art, where no such liquid-air interfaces exist.

As can be seen in FIG. 9A, the relief structure 9 avoids spilling of the liquid when the device is tilted. Because of the tilting process, the droplet that forms at the top of the well may increase in volume, or swell, but will not spill or overflow due to the relief structure provided.

Not shown in FIG. 9A are one or two optional reservoirs 12 arranged at one or two sides of the microcompartment device.

Figure 9B:
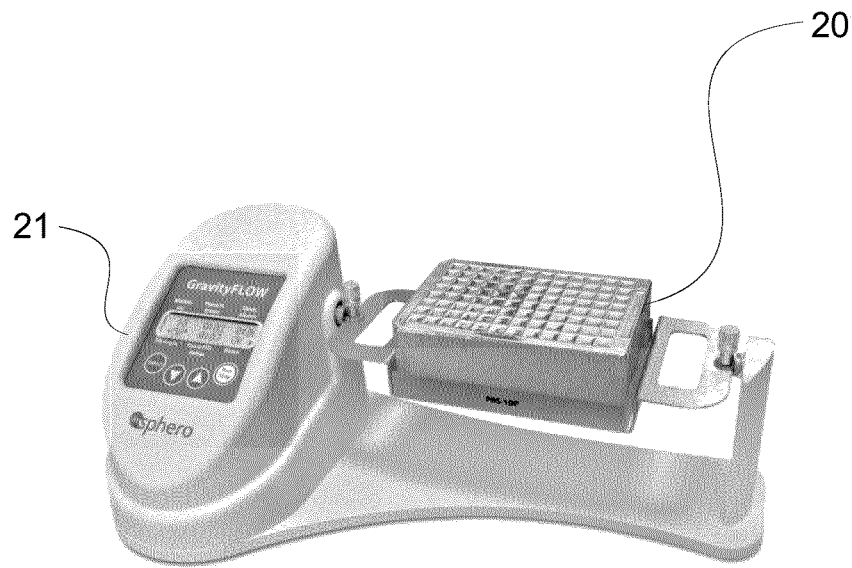

FIG. 9B shows a tilting device 21 that can be used to accommodate a frame structure 20, or strips or microtissue compartment devices according to the invention in general.

Figure 10A:
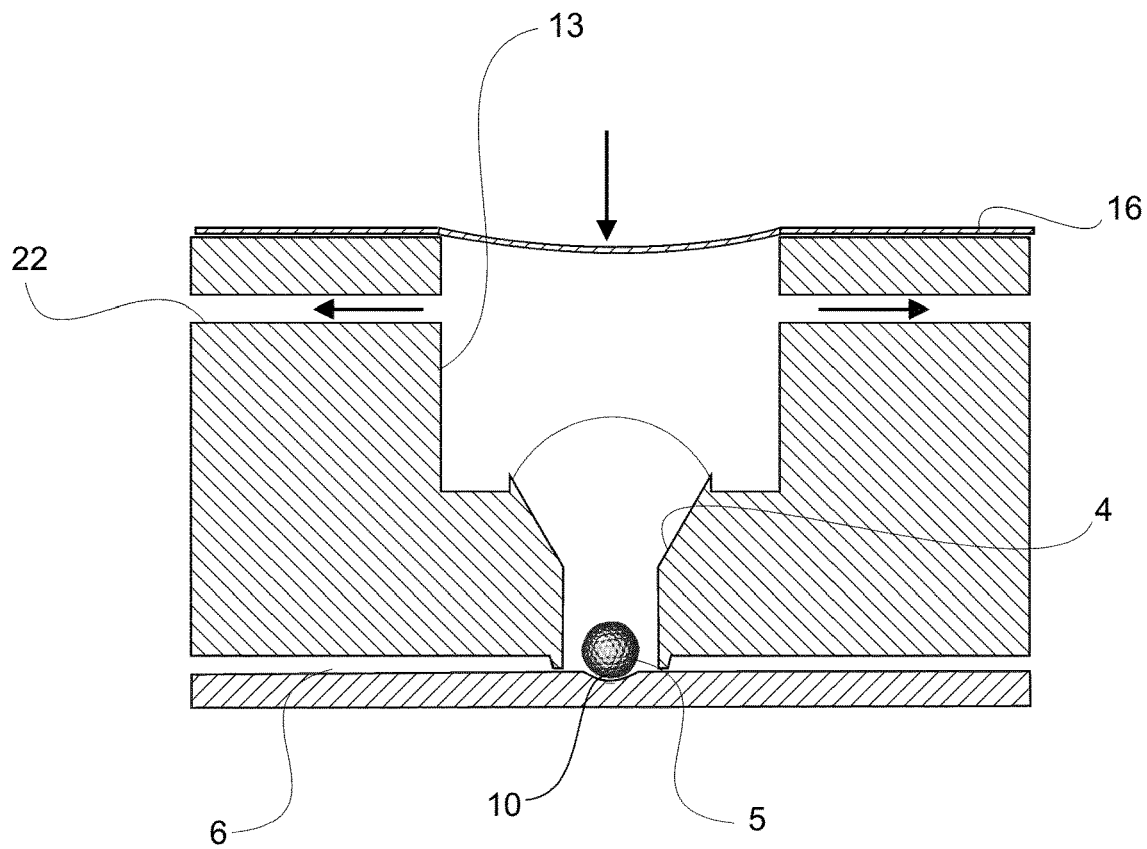
Figure 10B:
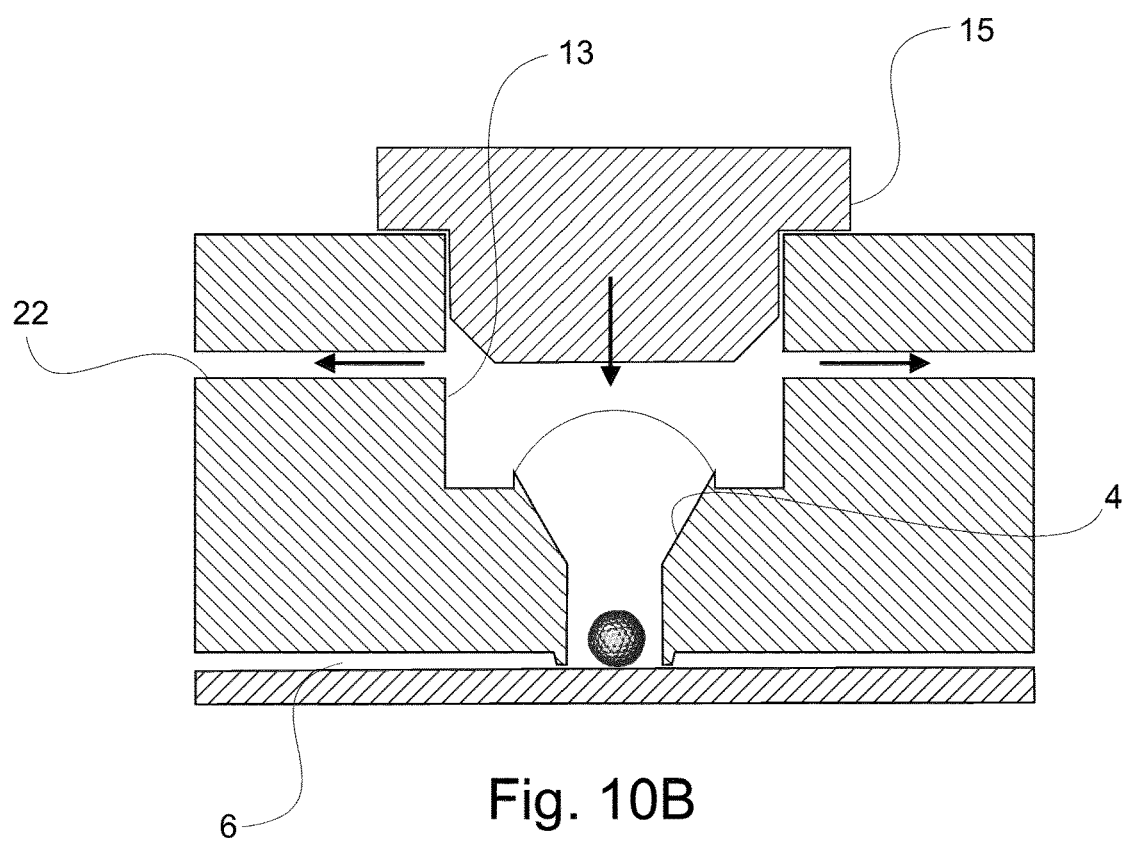

FIG. 10 shows the effect of the channels 22 connecting the compartments 13 above the wells 4 in an embodiment of the device which is either sealed by a sealing film 16 (FIG. 10A) or by a plug 15 (FIG. 10B).

When, in the absence of such channel, the sealing film, which may have a certain degree of elasticity, is poked inwards, e.g., during initial application or by sloppy of the device through an operator, gaseous medium may be pressed into the well 4 (see arrow) where it may either displace the microtissue 5, or develop bubbles in the conduit 6 fluidically connecting the wells to one another. The same can happen when the plug 15 is pressed into the space above the well. Both effects have undesirable consequences because either the microtissue can suffer, or the supply with culture media, washing media or test media is interrupted, or both.

The provision of a channel 22 connecting the compartments 13 above the wells 4 can help avoid this as it allows gaseous media to circulate between the different wells (see arrow), and allow pressure equilibration between the different spaces compartments above the wells. Essentially the same advantages apply when a plug 15 is used, as can be seen in FIG. 10A

REFERENCES

Kim et al. Journal of Biotechnology 205 (2015), 24-35
Kim et al. Journal of Laboratory Automation 20(3), 2015, 274-282
Maschmeyer, I. et al. Lab Chip 15, 2688-2699 (2015)
Ruppen, J. et al. Lab Chip 14, 1198-205 (2014)
Ruppen, J. et al. Lab Chip 15, 3076-3085 (2015)
Occhetta, P. et al. Sci. Rep. 5, 10288 (2015).
Kwapiszewska, K. et al. Lab Chip 14, 2096-2104 (2014)
Jin, H. J. et al. Trans. Korean Soc. Mech. Eng. A 35, 131-134 (2011)
Hsiao, A. Y. et al. Biomaterials 30, 3020-3027 (2009)
Torisawa, Y. et al. Biomaterials 28, 559-566 (2007)
Wu, L. et al. Biomed. Microdevices 10, 197-202 (2008)
Kijanska M and Kelm J., Assay Guidance Manual, 2016
Kelm J et al. Biotechnology and Bioengineering, 83(2) 173-180 (2003)

REFERENCE NUMBERS 1. compartment structure
2. upper surface
3. lower surface
4. well
4a. lower well section with a given diameter
4b. upper well section with an extended diameter
5. microtissue
6. conduit fluidically connecting at least two wells to one another
7. base structure
8. frame structure
9. relief structure that prevents spreading or overflow of a liquid volume comprised in said well
10. pit arranged concentrically to the well
11. lip structure
12. reservoir
13. space above the wells
14. grid spacing pattern
15. plug
16. sealing film
17. membrane in plug
18. liquid-air interface
19. strip
20. frame structure
21. titling device
22. channel connecting the spaces above the wells

What is claimed is:

1. A microtissue compartment device, comprising a compartment structure (1) having
   (i) an upper surface (2) and a lower surface (3), and
   (ii) at least two wells (4) suitable for accommodating one or more microtissues (5) in a liquid volume, each well having
      a) a lower section (4a) with a given diameter,
      b) coaxially oriented thereto an upper section (4b) with an extended diameter of the upper section, and
   (iii) at least one conduit (6) fluidically connecting the at least two wells to one another, and
   (iv) a plurality of compartments (13), wherein a compartment of the plurality of compartments is arranged above each respective well, each compartment of the plurality of compartments being defined by a respective outer wall and a lower surface,
   and wherein at least one well has, in its upper section, a relief structure (9) that prevents spreading or overflow of a liquid volume in said well into the compartment (13), wherein the relief structure comprises an overflow preventing edge that extends upwardly from the lower surface that defines the compartment arranged above the respective well,
   wherein at least one well has at least one lip structure (11), extending downward from the lower surface (3) of the compartment structure, which lip structure protrudes into the conduit and is configured to deflect liquid flowing through the conduit to cause the liquid to enter the well from a direction that deviates from a direction determined by a longitudinal axis of the conduit.

2. The device according to claim 1, wherein the outer wall of the compartment (13) above at least one well defines a first channel (22) connecting the compartment (13) above the at least one well to either another compartment (13) above a neighboring well or to an exterior.

3. The device according to claim 1, which further comprises a base structure (7) having an upper surface and a lower surface, which base structure is releasably or irreleasably attached to the lower surface of the compartment structure.

4. The device according to claim 1, wherein the at least one conduit (6) is provided in the compartment structure (1).

5. The device according to claim 4, wherein the at least one conduit consists, essentially, of a longitudinal furrow defined by two lateral walls.

6. The device according to claim 1, wherein the upper section of at least one well is essentially funnel-shaped, with the diameter thereof extending in an upward direction.

7. The device according to claim 1, wherein at least one well has an essentially elliptic or circular cross section.

8. The device according to claim 3, wherein the bottom structure of at least one well—either arranged in the compartment structure or in the base structure— has an elliptic or circular pit (10) arranged concentrically to the well.

9. The device according to claim 3, wherein the compartment structure or the base structure comprises at least one reservoir (12) fluidically connecting to at least one well by means of a conduit.

10. The device according to claim 1, wherein the lower section (4a) of at least one well has a diameter of between <3 mm and >0.3 mm.

11. The device according to claim 1, wherein the at least one conduit has a height of between <1 mm and >0.3 mm.

12. The device according to claim 1, wherein the device further comprises at least one row of 3 or more wells, being spaced apart from one another in a grid spacing pattern (14) of 9 mm, 4.5 mm or 2.25 mm.

13. The device according to claim 1, wherein the device further comprises one or more sealing structures for sealing the wells from their upper side,
   wherein the sealing structure is at least one selected from the group consisting of:
      a plug (15) inserted into the compartment (13) above the wells;
      a sealing film (16) attached to the upper surface of the compartment structure; and
      combinations thereof.

14. A strip (19) suitable for disposing in a frame structure that is compatible to the microtiter plate standard, said strip accommodating at least one microtissue compartment device or compartment structure according to claim 1.

15. A frame structure (20) compatible to the microtiter plate standard, said frame structure comprising at least one strip according to claim 14 or at least one microtissue compartment device or compartment structure having
- (i) an upper surface (2) and a lower surface (3), and
- (ii) at least two wells (4) suitable for accommodating one or more microtissues (5) in a liquid volume, each well having
  - a) a lower section (4a) with a given diameter,
  - b) coaxially oriented thereto an upper section (4b) with an extended diameter, and
- (iii) at least one conduit (6) fluidically connecting at least two wells to one another, and
- (iv) at least one space arranged above a well, the at least one space at least partially defined by a lower surface, and wherein at least one well has, in its upper section, a relief structure (9) that prevents spreading or overflow of a liquid volume comprised in said well into the space, wherein the relief structure comprises an overflow preventing edge that extends upwardly from the lower surface that at least partially defines the at least one space, wherein at least one well has at least one lip structure (11), extending downward from the lower surface (3) of the compartment structure, which lip structure protrudes into the conduit and in such way deflecting liquid flowing through the conduit to enter the well from a direction that deviates from the direction determined by the longitudinal axis of the conduit.

16. A model organism on a chip, said model organism comprising at least one microtissue compartment device or compartment structure according to claim 1, with two or more different microtissues arranged in the wells of the compartment device.

17. The model organism according to claim 16, wherein the microtissue is at least one selected from a group consisting of microtissue spheroid, organoid or precision cut tissue slice.

18. The device according to claim 2, wherein the outer wall of the compartment above the at least one well comprises an upper portion and a lower portion, wherein the lower portion of the outer wall of the compartment peripherally encloses a portion of an interior of the compartment, and wherein the upper portion of the outer wall of the compartment defines the first channel.

19. The device according to claim 18, wherein the upper portion of the outer wall of the compartment defines a second channel positioned on an opposing side of the outer wall from the first channel.

20. The device according to claim 1, wherein the outer wall of each compartment of the plurality of compartments comprises a first pair of opposing wall portions and a second pair of opposing wall portions that are perpendicular to or generally perpendicular to, and extend between, the first pair of opposing wall portions.

* * * * *